United States Patent
Roh et al.

(10) Patent No.: US 10,751,379 B2
(45) Date of Patent: Aug. 25, 2020

(54) METHOD FOR PREPARING ANTI-OBESITY COMPOSITION BY USING ASTRINGENT PERSIMMONS AND MANDARIN PEELS

(71) Applicant: INDUSTRY ACADEMIC COORPERATION FOUNDATION DAEGU HAANY UNIVERSITY, Gyeongsan-si, Gyeongsangbuk-do (KR)

(72) Inventors: Seong Soo Roh, Daegu (KR); Mi Rae Shin, Daegu (KR)

(73) Assignee: INDUSTRY ACADEMIC COORPERATION FOUNDATION DAEGU HAANY UNIVERSITY, Gyeongsan-Si, Gyeongsangbuk-Do (KR)

( * ) Notice: Subject to any disclaimer, the term of this patent is extended or adjusted under 35 U.S.C. 154(b) by 0 days.

(21) Appl. No.: 16/340,775

(22) PCT Filed: Dec. 28, 2016

(86) PCT No.: PCT/KR2016/015399
§ 371 (c)(1),
(2) Date: Apr. 10, 2019

(87) PCT Pub. No.: WO2018/070617
PCT Pub. Date: Apr. 19, 2018

(65) Prior Publication Data
US 2019/0282645 A1    Sep. 19, 2019

(30) Foreign Application Priority Data
Oct. 10, 2016   (KR) ........................ 10-2016-0130684

(51) Int. Cl.
*C12N 9/42* (2006.01)
*A61K 36/44* (2006.01)
(Continued)

(52) U.S. Cl.
CPC .............. *A61K 36/44* (2013.01); *A23L 19/00* (2016.08); *A23L 29/00* (2016.08); *A23L 33/00* (2016.08); *A23L 33/105* (2016.08); *A61K 9/19* (2013.01); *A61K 36/752* (2013.01); *A61K 47/36* (2013.01); *A61P 3/04* (2018.01)

(58) Field of Classification Search
CPC .................................................. C12N 9/2437
See application file for complete search history.

(56) References Cited

FOREIGN PATENT DOCUMENTS

| KR | 10-1383960 B1 | 4/2014 |
| KR | 10-1545504 B1 | 8/2015 |

(Continued)

OTHER PUBLICATIONS

International Search Report for PCT/KR2016/015399 dated Jul. 10, 2017 from Korean Intellectual Property Office.
(Continued)

*Primary Examiner* — Rosanne Kosson
(74) *Attorney, Agent, or Firm* — Paratus Law Group, PLLC

(57) ABSTRACT

Disclosed is a method for preparing an anti-obesity composition by using astringent persimmons and mandarin peels, the method comprising: adding a solvent to astringent persimmons and mandarin peels and then heating the same; degrading the extracted solution by using an enzyme; and filtering the solution degraded by the enzyme and then concentrating the filtered solution.

11 Claims, 3 Drawing Sheets

(51) Int. Cl.
  *A61P 3/04*    (2006.01)
  *A61K 9/19*    (2006.01)
  *A61K 36/752*   (2006.01)
  *A61K 47/36*    (2006.01)
  *A23L 19/00*    (2016.01)
  *A23L 33/00*    (2016.01)
  *A23L 33/105*   (2016.01)
  *A23L 29/00*    (2016.01)

(56) References Cited

FOREIGN PATENT DOCUMENTS

| KR | 10-2016-0032631 A | 3/2016 |
|---|---|---|
| KR | 10-1632580 B1 | 6/2016 |
| KR | 10-2016-0082824 A | 7/2016 |

OTHER PUBLICATIONS

Yeo, Eun Ju, "Effects of Jeju Circus Unshiu Peel Extract after Bioconversion with Cytolase on High Fat Diet-induced Obesity in Mouse Model", Myongji University Graduate School, Department of Food and Nutrition, 2014, pp. i-70.

Lim, Hee Jin et al., "Anti-Obesity Effects of Jeju Hallabong Tangor (*Citrus kiyomi x ponkan*) Peel Extracts in 3T3-L Adipocytes", Journal of the Korean Society of Food Science and Nutrition, 2014, pp. 1688-1694, vol. 43, No. 11.

Ojun Kwon et al., "Improving Effects on Rats with Reflux Esophagitis Treated with Combined Extract of Young persimmon fruit and Citrus peel", The Korea Journal of Herbology, 2016, pp. 25-31, vol. 31, No. 1.

Choi, Jun-Hyuk et al., "Development of value-added fat burning & immuno-stimulating food materials from agricultural by-products of *Jeju-do* citrus using bioconversion as green technology", Project Report sponsored by Ministry of Agriculture, Food and Rural Affairs, Jul. 18, 2015, pp. 1-380.

A

B

C

D

METHOD FOR PREPARING ANTI-OBESITY COMPOSITION BY USING ASTRINGENT PERSIMMONS AND MANDARIN PEELS

CROSS-REFERENCE TO PRIOR APPLICATIONS

This application is a National Stage Patent Application of PCT International Patent Application No. PCT/KR2016/015399 (filed on Dec. 28, 2016) under 35 U.S.C. § 371, which claims priority to Korean Patent Application No. 10-2016-0130684 (filed on Oct. 10, 2016), which are all hereby incorporated by reference in their entirety.

BACKGROUND

The present invention relates to a method for preparing an anti-obesity composition by using astringent persimmons and mandarin peels, and more particularly, to a method for preparing an anti-obesity composition by using astringent persimmons and mandarin peels, in which the composition is capable of reducing fat absorption by reducing an activity of pancreatic lipase, thereby having effects such as weight loss, a reduction of TC, TG and LDL-cholesterol, and a reduction of visceral fat.

The present invention draws a conclusion from a study carried out with the support of R&D Program for Forestry Technology provided by Korea Forest Service.

[Project no: 5121414L010100, title: Development and commercialization of an astringent persimmons for individual food ingredients through the identification of the function of body fat adjustment and the application of human body]

Obesity results from an energy imbalance is considered a serious global health risk by the WHO. It is also associated with health problems such as hyperlipidemia, hypertension, fatty liver disease, diabetes, cancers, osteoarthritis, and asthma. In 2014, WHO reported that 1.9 billion people, 31% of adults over 18 years and older, stated as obese. Moreover, WHO predicted that this number will be elevated to approximately 3.3 billion (about 1.7 times) by 2030. According to this the current trend, the economic burden of obesity (direct and indirect medical care costs including health monitoring, nutritional supplements, and surgical management) is expected to grow every year.

Pancreatic lipase is an enzyme responsible for digestion and absorption of dietary fat. Reduction in energy intake from dietary fat through inhibition of this enzyme may be a good strategy to prevent and treat obesity. Orlistat (Proprietary name, Xenial) approved by FDA is an effective drug for long-term treatment of obesity. This Orlistat exerts the drug efficacy through inhibition of pancreatic lipase enzyme and prevents the absorption of approximately 30% of dietary fat. However, it is limited in use due to severe gastrointestinal side effects. Thus, the recent obesity treatment targets are focused on innoxious and therapeutic natural products.

Korean Patent Application Laid-open Publication No. 2016-0082824 discloses a composition for improving lipid metabolism and anti-obesity comprising a mixture of bokbunja and red ginseng fermented extract as an active ingredient. The invention discloses an anti-obesity effect through improvement of lipid metabolism using a composition obtained by isolating bokbunja extract and red ginseng extract and then fermenting with lactic acid bacteria, but has disadvantages in that the composition has an anti-obesity effect only through improvement of lipid metabolism and cannot block the absorption of lipid which is the cause of obesity, and the price of red ginseng and bokbunja is relatively high, so that it is difficult to continue the long-term administration.

Korean Patent No. 1632580 discloses health functional food having an obesity inhibiting effect and a method for producing the same. The invention discloses a health functional food obtained by extracting from respectively processed ginger, maca, corn, mate leaf, and green tea leaf by heating, but has disadvantages in that the health functional food has an anti-obesity effect only through improvement of lipid metabolism and cannot block the absorption of lipid which is the cause of obesity, and it is difficult to be commercialized since each of the ingredients must be processed separately and a method of extracting is complicated.

SUMMARY

The present invention has been conceived in order to solve the above problem, and relates to a method for preparing an anti-obesity composition by using astringent persimmons and mandarin peels, the composition being capable of lowering the activity of pancreatic lipase to prevent degradation of dietary fat by pancreatic lipase, accordingly exhibiting effects such as weight loss, a reduction of TC, TG and LDL-cholesterol, and a reduction of visceral fat.

To solve the problem, the present invention provides a method for preparing an anti-obesity composition by using astringent persimmons and mandarin peels, the method including: step (a) for adding a solvent to astringent persimmons and mandarin peels and then heating the same; step (b) for degrading the extracted solution by using an enzyme; and step (c) for filtering the solution degraded by the enzyme and then concentrating the filtered solution.

In addition, the step (a) comprises performing extraction for 1 to 3 hours at a temperature of 80 to 120° C.

In addition, the solvent is at least one selected from among water, alcohol, benzene, toluene, carbon tetrachloride and IPA.

In addition, the step (a) is repeated 2 times.

In addition, the enzyme of the step (b) includes at least one selected from the group consisting of arabanase, cellulase, beta-glucanase, hemicellulase, and xylanase.

In addition, the step (b) is performed for 5-25 hours.

In addition, the filtration of the step (c) is performed using diatomite, activated carbon, zeolite or a hollow fiber membrane filter.

In addition, the filtering in step (c) is performed until the concentration of the extract reaches 0-10 BX.

In addition, the method further includes after the step (c), a step for adding a sterilized dextrin.

In addition, the method further includes a step for freeze-drying and pulverizing the extract.

In addition, the present invention provides an anti-obesity composition prepared using said preparing methods.

According to the present invention, the method for preparing an anti-obesity composition by using astringent persimmons and mandarin peels by which a pancreatic lipase inactive component contained in astringent persimmons and mandarin peels can be effectively extracted. The composition prepared by the preparing method reduces an activity of pancreatic lipase and inhibits the degradation and absorption of dietary fat, thus is useful for effective weight management.

DETAILED DESCRIPTION

Figure 1:
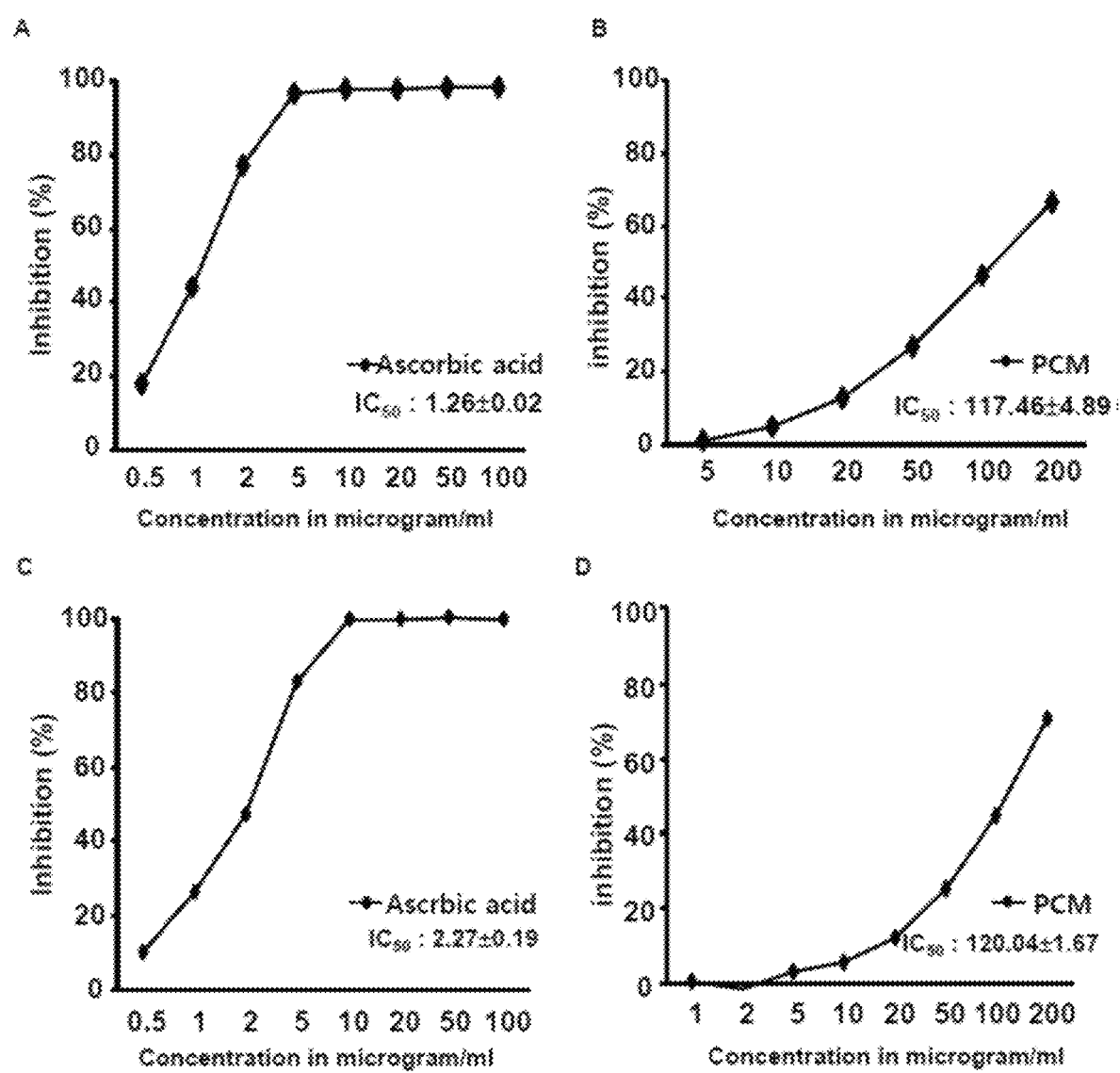
FIG. 1 shows DPPH and ABTS inhibition test results using PCM and ascorbic acid according to the present invention, A and B are graphs of DPPH test results, and C and D are graphs of ABTS test results.

Hereinafter, the present invention will be described in more detail through the preferred embodiments of the present invention. In explanation of the present invention, a detailed explanation thereof will be omitted when it is determined that a specific explanation of the related known art may blur the main idea of present invention. Throughout the description, when any part "includes/comprises" a certain component, which means that any part may further include/comprise other components, not exclude other components, unless otherwise specially stated.

The present inventors have noted that the reduction in the activity of pancreatic lipase by conventional chemical synthesis and the method of inhibiting fat absorption by the same cause serious gastrointestinal diseases and excessive cost. As a result of efforts to solve this problem, it was found that extracts of pancreatic lipase inactivation components can be extracted from the natural products, astringent persimmons and mandarin peels which are easily obtainable from the surroundings, thereby leading to the present invention.

Accordingly, the present invention relates to a method for preparing anti-obesity composition by using astringent persimmons and mandarin peels, the method including: step (a) for adding a solvent to astringent persimmons and mandarin peels and then heating the same; step (b) for degrading the extracted solution by using an enzyme; and step (c) for filtering the solution degraded by the enzyme and then concentrating the filtered solution.

The step (a) is a step of softening astringent persimmons and mandarin peels by heat to extract an active ingredient of the astringent persimmons and mandarin peels, a solvent to extract the active ingredient can be used without limitation, but preferably at least one selected from among water, alcohol, benzene, toluene, carbon tetrachloride and IPA can be used. In addition, since the composition of the present invention is administered to a human or animal, the active ingredient is expected to be water-soluble, and more preferably water can be used.

In addition, the step (a) is preferable to heat at a temperature of 80 to 120° C. for 1 to 3 hours such that the active ingredient elute as much as possible, and softens the astringent persimmons and mandarin peels, and more preferably at a temperature of 100° C. for 2 h. In addition, when the step (a) is performed only once, the enzyme degradation of the next step is not completely performed due to insufficient softening, therefore, it is preferable to repeat the step (a) several times, and more preferable to repeat 2 times in order to save time and cost consumption by the fuel used.

In the present invention, an astringent persimmon is, for example, an astringent persimmon of 3 to 10 cm in diameter with immature astringent taste persimmon and green appearance, and which is harvested 6 to 9 months after cultivation. The present invention uses an active ingredient such as polyphenols having an anti-obesity component extracted from persimmon and mandarin peels, and thus, it is preferable to use an astringent persimmon which is expected to have a high content of polyphenol. In addition, when an astringent persimmon is completely matured, the sugar content increases, thereby being difficult to lower the sugar content in concentration process, and sugar-induced weight gain may occur, therefore it is preferable to use an immature astringent persimmon.

The step (b) is a step of degrading by adding an enzyme to softened astringent persimmons and mandarin peels solution, and the enzyme to be used preferably includes at least one selected from the group consisting of arabanase, cellulase, beta-glucanase, hemicellulase, and xylanase, and more preferably Viscozyme from Novozymes (Denmark) is used to effectively degrade the astringent persimmon and mandarin peel composed of various components. In addition, it is preferable to carry out the degradation by enzyme for 5 to 25 hours so that the astringent persimmon and mandarin peel can be sufficiently degraded, more preferably 10 to 20 hours, and most preferably 15 hours. In addition, after completion of the degradation by the enzyme, it is preferable to inactivate the enzyme by heating to 80 to 100° C. in order to prevent side reactions such as saccharification by the enzyme and degradation of the active ingredient.

The step (c) is a step of removing dietary fiber, cell wall and the like excluding the active ingredient after the effective ingredient is eluted, and filtration is preferably performed using diatomite, activated carbon, zeolite or a hollow fiber membrane filter, and more preferably using diatomite which is a filter usable for foods.

In addition, it is preferable to concentrate the filtered solution reaches 0 to 10 BX. Since the composition of the present invention is used for alleviating obesity, it is preferable to concentrate to reach 0 to 10 BX to prevent sugar-induced weight gaining, and more preferably 0 BX.

The unit "BX" used herein is a unit for measuring sugar content and is often expressed as Brix. This is expressed as sugar content based on the concentration of sugarcane sugar dissolved in 100 g of water, as the value increases, it means that the more sugar is contained.

The present invention may further include, after the step (c), a step for adding sterilized dextrin. Dextrin is added to increase the viscosity of the produced composition and may be added for convenience of transportation and storage of the product. Also, the dextrin may be sterilized at 95° C. for 30 minutes to prevent a denaturing of the extract.

The present invention may further include a step for freeze-drying and pulverizing the extract. Since the produced composition is in a liquid phase, it may easily denatured and may not be easy to transport and store due to heavy weight. Therefore, it is preferable to freeze-dry and then pulverize into a powder form.

In addition, the present invention provides an anti-obesity composition prepared by the above-mentioned method.

Hereinafter, the present invention will be described through the particular examples.

EXAMPLES

Used Raw Materials

Porcine pancreatic lipase (Type 2), Orlistat, morpholinepropanesulphonicacid (MOPS), Tris-HCl, and p-nitrophenyl butyrate (p-NPB), 2,2-diphenyl-1-picrylhydrazyl (DPPH) and 2,2"-azino-bis-diammonium salt (ABTS) were purchased from Sigma-Aldrich Co. (St Louis, Mo., USA).

Ethylenediaminetetraacetic acid (EDTA) was purchased from Wako Pure Chemical Industries, Ltd. (Osaka, Japan).

Viscozyme was purchased from Novozymes (Denmark).

All other reagents were used as biochemical grade.

Treatment of Experimental Animals

Male healthy 4-week-old ICR mice (about 30-32 g) were purchased from Orient (Gyeonggi-do, Korea). Each mouse was kept at room temperature (22±3° C.) and humidity (55±5%) with a 12-h light/dark cycle. The experiments were approved by the Ethics Committee of Animal Experimentation of the University of Daegu Haany. The mice were allowed free access to laboratory pellet chow and water ad libitum.

After adaptation (1 week), all experimental mice except normal mice (n=8) were fed with 60% high-fat diet (HFD; Diet 12492, Research Diets, Inc., 105 New Brunswick, N.J., USA) for 5 days to adapt to a feed. Thereafter, ICR mice (n=32) fed 60% HFD were randomly divided into four groups (HFD control group, orlistat group, and two PCM treatment groups (50 and 200 mg/kg/day))(in each group n=8). The normal group is supplied with a normal feed and the rest of the groups are supplied with 60% HFD until the end of experiment.

The normal and HFD control groups were given water using a stomach tube, while the drug treatment groups were orally given Orlistat or PCM daily using a stomach tube for 6 weeks. After administration for 6 weeks, each mouse was sacrificed after fasting for 12 hours. The blood was immediately centrifuged for 10 minutes at 4° C.

Serum triglyceride and total cholesterol were conducted spectrophotometrically using commercially available kits (Wako Pure Chemical Industries, Ltd., Osaka, Japan). HDL-cholesterol is measured using a commercial kit from Asan Pharm Co., Ltd. (Hwaseong-si, Korea, Cat AM203). LDL-cholesterol levels are calculated though TG, TC and HDL levels, and the following formula.

LDL-cholesterol level (mg/dL)=[TC−(HDL-cholesterol)−TG]/5

Statistical Processing

All results are expressed as mean±standard error (mean±S.E). One-way analysis of variance (ANOVA) in accordance with Dunnett's multiple comparison test (SPSS 18.0 for Windows, SPSS Inc., U.S.A.) for a significance test was performed. When P<0.05, it was determined to be statistically significant.

Example 1

Astringent persimmon (*Diospyros kaki* Thunb.) was harvested (an astringent persimmon harvested of 3 to 10 cm in diameter with green color harvested at 6-8 months after cultivation) in Gyeongsangbuk-do Agricultural Research & Extension Services (Sangju, Korea) and a dried mandarin peel (Citrus unshiu. S. Marcov.) was purchased from MSC Co., Ltd. (Yangsan, Korea). Each 500 kg was selected and extracted with water and boiled in 100° C. for 2 hours for 2 times. Thereafter enzyme (Viscozyme) degradation was performed for 15 hours. Next, enzyme was inactivated in 90° C. for 30 minutes. After filtration using the diatomite, the extracts were concentrated to reach 0 Bx. The concentrated extracts were added dextrin and were sterilized in 95° C. for 30 minutes. The sterilized extracts were freeze-dried and pulverized by a grinder (the resultant was named as PCM).

Comparative Example 1

The extract was prepared in the same manner as in Example 1 except that an enzymatic degradation process was not performed.

Comparative Example 2

The extract was prepared in the same manner as in Example 1 except that enzymatic degradation process was performed for 5 hours.

Comparative Example 3

The extract was prepared in the same manner as in Example 1 except that enzymatic degradation process was performed for 25 hours.

Experimental Example 1

Antioxidant activity determination of PCM was performed by inhibition of by DPPH radical according to the method of Park et al. 100 μL of an ethanolic solution of PCM (blank: 100 μL of ethanol) was added to 100 μL of an ethanolic solution of DPPH (60 μM) using 96-well plate. The ascorbic acid (standard sample) was prepared for eight concentrations (0.5, 1, 2, 5, 10, 20, 50, and 200 μg/mL). The reaction mixture was stored in the dark at 25° C. for 30 minutes. The optical density was determined using a microplate reader (M200 PRO, Tecan, Austria). The mixture was measured spectrophotometrically using 540 nm. The antioxidant activity of each sample was expressed in terms of $IC_{50}$ (micromolar concentration required to inhibit DPPH radical formation by 50%, calculated from the log-dose inhibition curve). Antioxidant activity was expressed in terms of $IC_{50}$, and a lower $IC_{50}$ value corresponds to a large inhibition. The radical scavenging activity was calculated using the following formula.

DPPH radical scavenging activity (%)=[1($A_{sample}$/$A_{blank}$)]×100

As shown in FIG. 1 (A, B), $IC_{50}$ of DPPH inhibition of the PCM was 117.46±4.89 μg/mL, and $IC_{50}$ value of ascorbic acid (positive control) was 1.26±0.02 μg/mL.

Experimental Example 2

ABTS inhibition of the different extracts was measured according to the modified method of Park et al. ABTS stock solution was dissolved in water to 7.4 mM concentration. The ABTS radical cation (ABTS) was produced by reacting ABTS stock solution with 2.45 mM potassium persulfate and allowing the mixture to stand for 14 hours at room temperature in the dark. The ABTS solution was diluted with ethanol to obtain an absorbance of 0.70±0.02 at 750 nm. After adding diluted ABTS solution to PCM solution, the mixture was left standing at room temperature for 15 minutes in the dark. The ascorbic acid (standard sample) was prepared for eight concentrations (0.5, 1, 2, 5, 10, 20, 50, and 200 μg/mL). The absorbance at 750 nm was measured using a microplate reader (M200 PRO, Tecan, Austria). The blank was prepared in the same manner, except that distilled water was used instead of the sample. The radical scavenging activity was calculated using the following formula.

ABTS radical scavenging activity (%)=[1($A_{sample}$/$A_{blank}$)]×100

$IC_{50}$ value of PCM against the ABTS was 120.04±1.67 μg/mL and $IC_{50}$ value of ascorbic acid as a positive control was 2.27±0.19 μg/mL (FIG. 1 (C, D)).

Experimental Example 3

Pancreatic lipase activity was modified from the method previously reported by Kim et al. Briefly, an enzyme buffer was prepared by the addition of 6 μL of a solution of porcine pancreatic lipase in buffer containing 10 mM of MOPS (morpholinepropanesulfonic acid) and 1 mM of EDTA, pH 6.8, to 169 μL Tris buffer (100 mM Tris-HCl and 5 mM $CaCl_2$, pH 7.0). Then, either 20 μL of PCM of Example 1 at the test concentration (100, 250, 500, and 1000 μg/mL) or orlistat (0.1, 0.25, 0.5, and 1 μg/mL) was mixed with 175 μL of enzyme buffer and left standing for 15 minutes at 37° C. with 5 μL of the substrate solution (10 mM p-NPB (p-nitrophenyl butyrate) in dimethylformamide). The enzymatic reactions were allowed to proceed for 35 minutes at 37° C. Lipase activity was determined by measuring the hydrolysis of p-NPB into p-nitrophenol. Increase in light absorption at 405 nm was measured using a microplate reader (M200 PRO, Tecan, Austria). Inhibition of lipase activity was expressed as the percentage decrease in OD when porcine pancreatic lipase was incubated with the test compounds. Lipase inhibition was calculated according the following formula.

Inhibition (%)=100−[(B−b)/(A−a)*100]

Where A is the activity without inhibitor, a is the negative control without inhibitor, B is the activity with inhibitor, and b is the negative control with inhibitor, and the results were expressed as an average (n=4).

Figure 2:
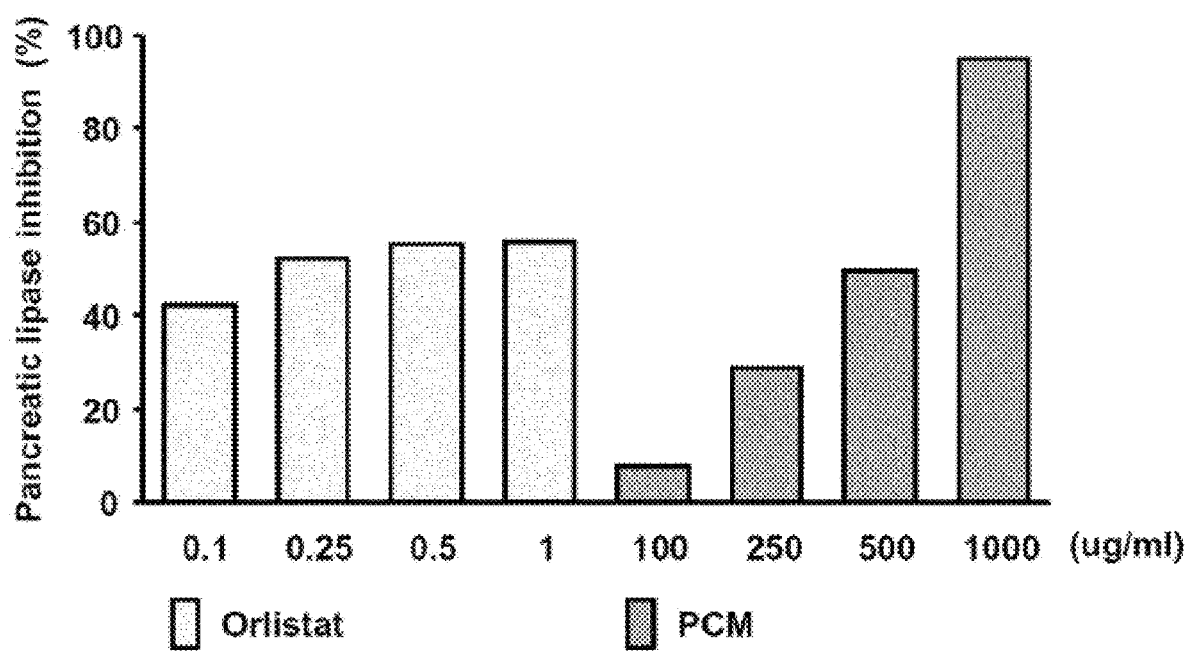
FIG. 2 shows a graph of pancreatic lipase inhibition according to the present invention.

As shown in FIG. 2, the lipase inhibition of Orlistat did not rise at least a certain concentration, but the higher the dose of PCM, the higher the lipase inhibition.

Experimental Example 4

The total phenolic content of PCM was quantified by mild modification from the method of Folin-Ciocalteu. 10 μL PCM of Example 1 and 790 μL of distilled water were mixed and added to well and then mixed with 50 μL of Folin-Ciocalteu's reagent for 1 minute. After that 150 μL of 20% sodium carbonate solution ($Na_2CO_3$) was added and the mixture was mixed for 2 hours at 20° C. Lastly, the absorbance of the resulting color was measured at 765 nm. The total phenolic content was expressed as mg gallic acid equivalents per gram extract. Values presented are the average of three measurements. Flavonoid was extracted and quantified by adaptation of the method of Lister et al. 50 μL of PCM and 500 μL of diethylene glycol were mixed in well. And then 1 N NaOH 5 μL was added and the mixture was left standing for 1 hour at 37° C. Finally, the absorbance of the resultant was measured at 420 nm. The flavonoid content was expressed as mg naringin equivalents per gram extract. Values presented are the average of three measurements.

Total phenolic content was measured as gallic acid equivalents (GAE) with reference to standard curve (y=0.023x+0.30 and R2=0.997) and was 29.90±0.14 mg GAE/g of PCM extract. The flavonoid content was 18.33±0.08 mg naringin equivalent/g of PCM extract, with reference to standard curve (y=0.0195x+196 0.04 and R2=0.9999).

Experimental Example 5

To analyze the effects of PCM on HFD-induced obesity, the development of HFD-induced obesity in mice with and without PCM prepared in Example 1 supplementation for 6 weeks was investigated, and measured the effects of PCM on serum lipid profiles such as TG, TC, HDL-cholesterol, and LDL-cholesterol, after the experiment.

Figure 3:
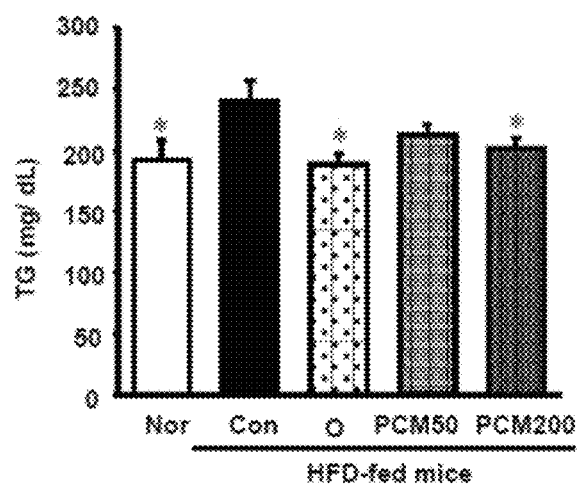
FIG. 3 shows a graph respectively showing TG, TC, HDL-cholesterol, and LDL-cholesterol levels of mice of each experimental group after 6 weeks experiment according to the present invention.
Figure 3:
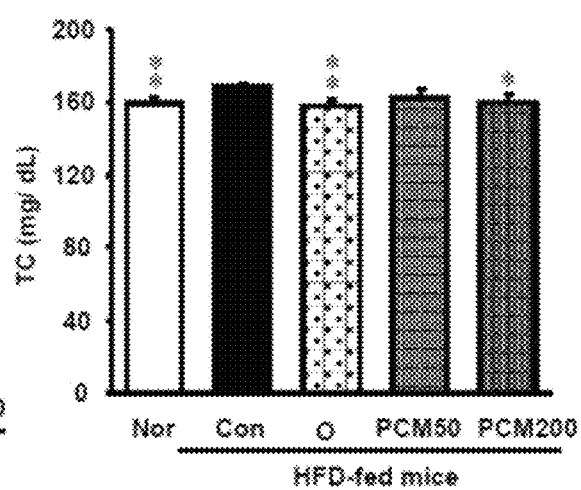
Figure 3:
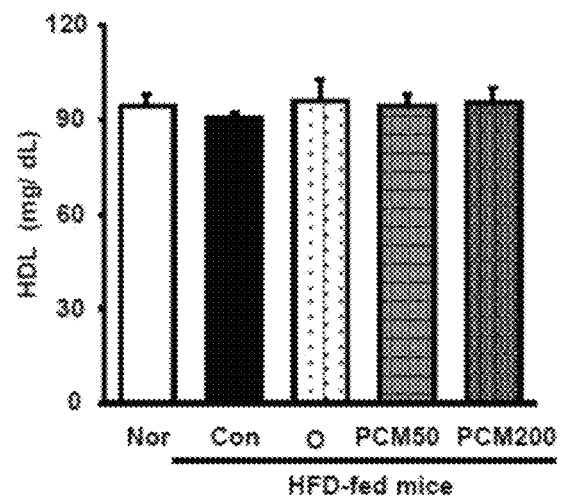
Figure 3:
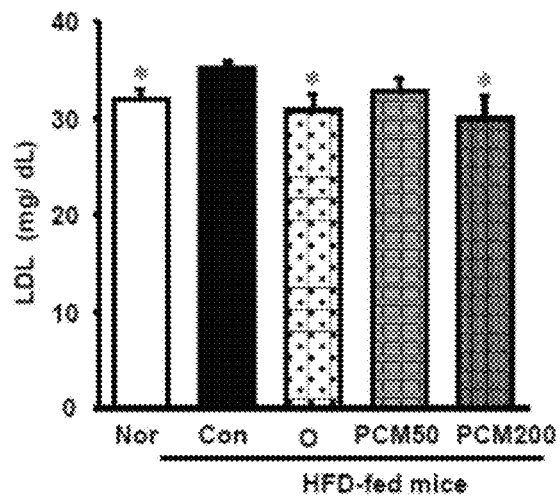

As shown in FIG. 3, TG, TC, and LDL-cholesterol levels in mice (Con) after 6 weeks of HDF-supplied were significantly higher than normal food supplied mice (Nor). Orlistat-supplied mice (0) or 200 mg of PCM-supplied mice (PCM200) were at the same level as normal food-supplied mice, and this shows that both Orlistat and PCM may help to lower the TG, TC and LDL-cholesterol levels. In addition, mice (PCM50) supplied with 50 mg of PCM shows a reduction in certain amount of level not as much as Orlistat or PCM200. In addition, HDL-cholesterol which is known to be beneficial to vascular health, was not significantly changed in all mice.

Experimental Example 6

To analyze the effects of PCM on HFD-induced obesity, the development of HFD-induced obesity in mice with and without PCM prepared in Example 1 supplementation for 6 weeks was investigated, and measured the change in body weight and visceral fat, after the experiment.

TABLE 1

| Group | | Initial (g) | Final (g) | Weight Amount of change (g/6 weeks) | Amount of Visceral fat (g) |
|---|---|---|---|---|---|
| | General food | 36.06 ± 0.96 | 47.92 ± 1.46 | 11.86 ± 1.00 | 24.10 ± 1.0 |
| HDF food | CON | 37.67 ± 0.51 | 55.15 ± 1.78 | 17.48 ± 1.95 | 57.5 ± 1.5 |
| | O | 36.71 ± 0.96 | 44.92 ± 1.62 | 8.21 ± 1.82 | 42.5 ± 2.8 |
| | PCM50 | 37.18 ± 0.44 | 48.06 ± 0.17 | 10.88 ± 0.52 | 50.6 ± 3.2 |
| | PCM200 | 36.93 ± 0.38 | 45.98 ± 0.94 | 9.05 ± 0.90 | 50.3 ± 2.3 |

As shown in Table 1, HFD control mice (CON) increased significantly final body weight compared with normal mice (Normal food) (55.15±1.78 g, 47.92±1.46 g). In addition, the visceral fat weight in HFD control mice was significantly increased compared to normal mice (238% of normal mice), but Orlistat and PCM200-treated mice (0, PCM200) were significantly decreased compared with those of HFD control mice. PCM50 treatment showed a tendency to decrease without significance. Above all, body weight change reduced significantly in all drug-treated experimental groups. Overall, PCM may help to alleviate the disorders of HFD-induced obesity.

Experimental Example 7

In order to check the effect according to the method for preparing PCM, experiments were performed in the same manner as in Experimental Example 6 using PCM respectively prepared by the methods of Example 1, Comparative Example 1, Comparative Example and Comparative Example 3. 200 mg of PCM prepared by each method was supplied to experimental mice, and changes of body weight and changes visceral fat according to the preparing method were measured.

TABLE 2

| Group | | Viscozyme degradation time | Weight | | | Amount of Visceral fat (g) |
| --- | --- | --- | --- | --- | --- | --- |
| | | | Initial (g) | Final (g) | Amount of change (g/6 weeks) | |
| General food | | — | 36.06 ± 0.96 | 47.92 ± 1.46 | 11.86 ± 1.00 | 24.1 ± 1.0 |
| HDF food | CON | — | 37.67 ± 0.51 | 55.15 ± 1.78 | 17.48 ± 1.95 | 57.5 ± 1.5 |
| | Example 1 | 15 hours | 36.93 ± 0.38 | 45.98 ± 0.94 | 9.05 ± 0.90 | 50.3 ± 2.3 |
| | Comparative Example 1 | 0 hour | 36.51 ± 0.36 | 53.36 ± 1.42 | 16.85 ± 1.65 | 54.8 ± 1.8 |
| | Comparative Example 2 | 5 hours | 38.38 ± 0.54 | 49.16 ± 0.52 | 10.78 ± 1.02 | 52.1 ± 3.2 |
| | Comparative Example 3 | 25 hours | 36.03 ± 0.48 | 51.02 ± 1.02 | 14.99 ± 1.32 | 55.2 ± 2.1 |

As shown in Table 2, it was showed that the Comparative Example 1 exhibited the least effect due to no degradation by Viscozyme, and it was understood that the Comparative Example 2 could not be eluted an active ingredient sufficiently due to short degradation time by Viscozyme. In addition, Comparative Example 3 has sufficient elution time by the Viscozyme, but the eluted active ingredient was degraded by the enzyme or was inactivated by binding with the enzyme, thereby being judged that the effects wears off.

Hereinbefore, preferred embodiments of the present invention have been explained in detail. The explanation of the present invention is only for illustration, and it could be understood that particular embodiment could be easily changed without changing the technical spirit or essential features of the present invention by one of ordinary skilled in the art.

Accordingly, it should be interpreted that the scope of the present invention is represented by claims hereinafter rather than the detailed explanation, and all changes or modifications derived from the meaning, range and equivalent concept of claims are included in the scope of the present invention.

The invention claimed is:

1. A method for preparing an anti-obesity composition by using astringent persimmons and mandarin peels, the method comprising:
   step (a) for adding a solvent to astringent persimmons and mandarin peels and then heating the same;
   step (b) for degrading the extracted solution by using an enzyme; and
   step (c) for filtering the solution degraded by the enzyme and then concentrating the filtered solution.

2. The method according to claim 1, wherein the step (a) comprises performing extraction for 1 to 3 hours at a temperature of 80 to 120° C.

3. The method according to claim 1, wherein the solvent is at least one selected from the croup consisting of water, alcohol, benzene, toluene, carbon tetrachloride and isopropyl alcohol (IPA).

4. The method according to claim 1, wherein the step (a) is repeated 2 times.

5. The method according to claim 1, wherein the enzyme of the step (b) includes at least one selected from the group consisting of arabanase, cellulase, beta-glucanase, hemicellulase, and xylanase.

6. The method according to claim 1, wherein the step (b) is performed for 5-25 hours.

7. The method according to claim 1, wherein the filtration of the step (c) is performed using diatomite, activated carbon, zeolite or a hollow fiber membrane filter.

8. The method according to claim 1, wherein the filtering in step (c) is performed until the concentration of the extract reaches 0-10 BX.

9. The method according to claim 1, further comprising, after the step (c), a step for adding a sterilized dextrin.

10. The method according to claim 1, further comprising a step for freeze-drying and pulverizing the extract.

11. An anti-obesity composition prepared according to claim 1.

* * * * *